United States Patent
Kumar et al.

(10) Patent No.: US 7,547,791 B2
(45) Date of Patent: Jun. 16, 2009

(54) ONE-POT PROCESS FOR THE PREPARATION OF ANTIEMETIC AGENT, 1,2,3,9-TETRAHYDRO-9-METHYL-3[(2-METHYL)-1H-IMIDAZOLE-1-YL)METHYL]-4H-CARBAZOL-4-O

(75) Inventors: Ashok Kumar, Maharashtra (IN); Dharmendra Singh, Maharashtra (IN); Atul Jadhav, Maharashtra (IN); Navinchandra Darpan Pandya, Maharashtra (IN); Shankar Deepak Panmand, Maharashtra (IN); Ramsingh Gajendrasingh Thakur, Maharashtra (IN)

(73) Assignee: IPCA Laboratories Ltd., Mumbai (IN)

( * ) Notice: Subject to any disclaimer, the term of this patent is extended or adjusted under 35 U.S.C. 154(b) by 0 days.

(21) Appl. No.: 11/666,330

(22) PCT Filed: Oct. 26, 2004

(86) PCT No.: PCT/IN2004/000336

§ 371 (c)(1), (2), (4) Date: Apr. 26, 2007

(87) PCT Pub. No.: WO2006/046253

PCT Pub. Date: May 4, 2006

(65) Prior Publication Data

US 2008/0009635 A1 Jan. 10, 2008

(51) Int. Cl.
C07D 233/00 (2006.01)

(52) U.S. Cl. .................. 548/335.1; 548/300.1

(58) Field of Classification Search .............. 548/300.1, 548/335.1
See application file for complete search history.

(56) References Cited

U.S. PATENT DOCUMENTS

| 4,695,578 A | 9/1987 | Coates et al. |
| 2002/0107275 A1 | 8/2002 | Lidor-Hadas et al. |
| 2004/0181076 A1 | 9/2004 | Hesoun et al. |
| 2004/0198794 A1 | 10/2004 | Westheim et al. |

OTHER PUBLICATIONS

Armarego, W.L.F.; Perrin, D.D. (1997). Purification of Laboratory Chemicals (4th Edition). Elsevier. Online version available at: www.knovel.com/knovel2/Toc.jsp?BookID=489&VerticalID=0.*

* cited by examiner

*Primary Examiner*—Kamal A Saeed
*Assistant Examiner*—Samantha L Shterengarts
(74) *Attorney, Agent, or Firm*—Blank Rome LLP

(57) ABSTRACT

A one-pot industrial process for preparing 1,2,3,9-tetrahydro-9-methyl-3-[(2-methyl-1H-imidazole-1-yl)methyl]-4H-carbazol-4-one of Formula-(I) from 1,2,3,9-tetrahydro-9-methyl-4H-carbazol-4-one of Formula-(IV) involves reaction of Formula (IV) with $HNR_1R_2$ salt and paraformaldehyde, where $R_1, R_2$ are independently alkyl groups or together forms a cyclic alkyl group, in a solvent system of acetic acid and hydrocarbon solvent to form a crude mixture of intermediate compounds of Formula (III) and (VIII), which is converted to ondansetron (Formula (I)) without isolation by reaction with 2methyimidazole in a suitable solvent system in the same pot.

29 Claims, No Drawings

ONE-POT PROCESS FOR THE PREPARATION OF ANTIEMETIC AGENT, 1,2,3,9-TETRAHYDRO-9-METHYL-3[(2-METHYL)-1H-IMIDAZOLE-1-YL) METHYL]-4H-CARBAZOL-4-O

TECHNICAL FIELD OF INVENTION

This invention relates to an industrial one-pot process for the preparation of 1,2,3,9-tetrahydro-9-methyl-3-[(2-methyl)- 1H-imidazole-1-yl)methyl]-4H-carbazol-4-one (Ondansetron) starting from 1,2,3,9-tetrahydrocarbazole-4-one, in high yield and purity.

BACKGROUND AND PRIOR ART

Ondansetron is a pharmaceutically active agent commonly used for the treatment of nausea and vomiting, particularly associated with chemotherapy in cancer treatments. In currently marketed pharmaceutical compositions, ondansetron is used as free base in rapidly dissolvable tablets and as hydrochloride salt in injections, tablets and oral solutions. The chemical name of Ondansetron is 1,2,3,9-tetrahydro-9-methyl-3-[(2-methyl)-1H-imidazole-1-yl)methyl]-4H-carbazol-4-one and is represented by the structural formula given below:

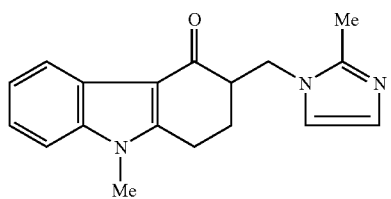

Formula I

Because Ondansetron molecule has a chiral carbon atom, it exists in two enantiomeric forms; however, racemic ondansetron is marketed so far. The molecule was first disclosed in the U.S. Pat. No. 4,695,578 in 1987. The '578 patent discloses many ways to prepare Ondansetron starting from a compound of general Formula II which in turn is prepared from 1,2,3,9-tetrahydro-9-methyl-4H-carbazole.

In another alternative, Ondansetron is prepared by N-methylation of 1,2,3,9-tetrahydro-3-[(2-methyl-1H-imidazol-1-yl)methyl]-4H-carbazol-4-one of Formula-VI with strong base like sodium hydride

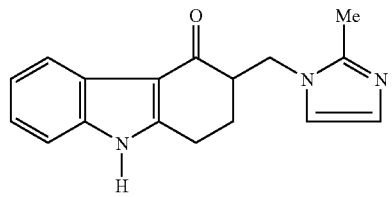

Formula VI and dimethylsulfate in solvents such as dimethyl formamide, THF or an aromatic hydrocarbon, toluene etc. The yield of this reaction is only about 21% since the activation of the ring nitrogen atom is difficult.

Yet another alternative preparation of Ondansetron is by Michael-type addition reaction of 2-methylimidazole to 9-methyl-3-methylene-1,2,3,9-tetrahydro-4H-carbazol-4-one of Formula-VIII which according to this patent is prepared from 3-[(trimethylamino)-methyl-1,2,3,9-tetrahydro-9-methyl]-4H-carbazol-4-one iodide (Formula VII) (Scheme II).

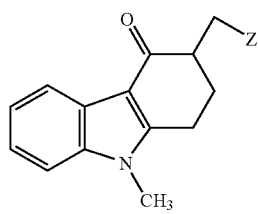

Formula II

Z is a reactive species

In one alternative, Ondansetron was prepared from hydrochloride salt of 3-[(dimethylamino)-methyl]-1,2,3,9-tetrahydro-9-methyl-4H-carbazol-4-one of Formula-III by treating it with 2-methyl imidazole in a medium of solvent such as water or an alcohol or their mixture thereof at reflux temperatures for longer period of time like 20 to 47 hours. (Scheme 1)

Scheme 1

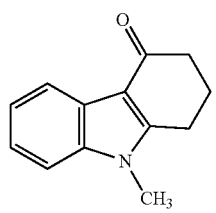

Formula IV

| paraformaldehyde
| dimethylamine hydrochloride
| Glacial acetic acid

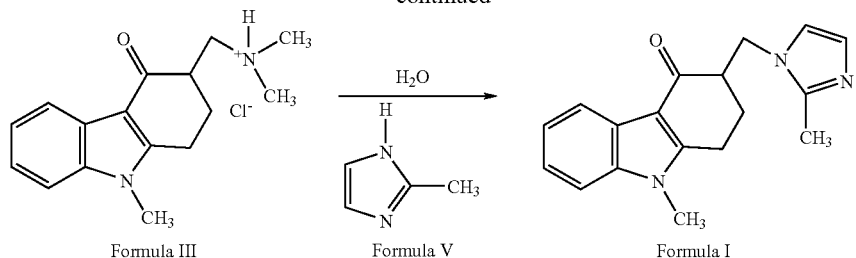
The Starting compound of Formula-III was prepared by a Mannich reaction of 1,2,3,9-tetrahydro-9-methyl-4H-carbazole with N,N-dimethylamine hydrochloride and paraformaldehyde in a medium of glacial acetic acid at reflux temperature for long duration to give Formula III in very poor yields.
Scheme II
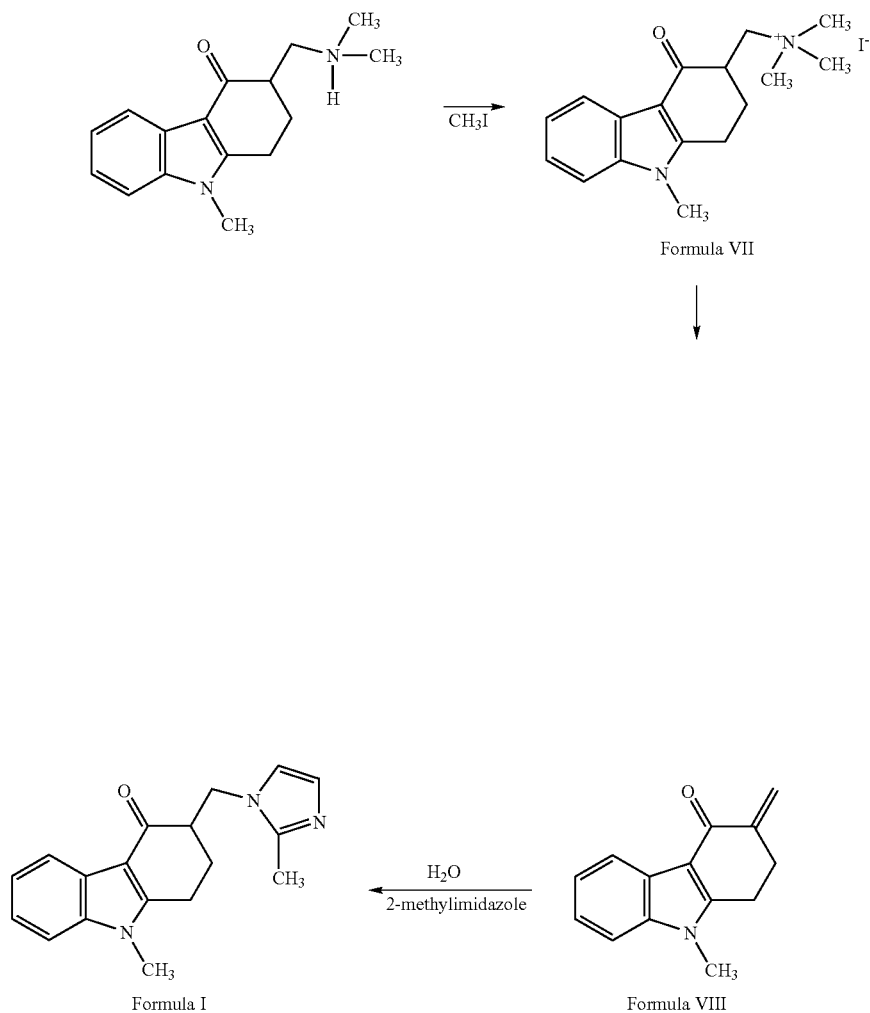

This particular reaction is carried out in solvent systems such as water, ethyl acetate, ketone e.g. acetone, MIBK and amides over a period of 20 hours resulting in 44% yield.

Yet another process disclosed in '578 is a substitution of chlorine in 3-(chloromethyl)-1,2,3,9-tetrahydro-9-methyl-4H-carbazol-4-one of Formula IX using 2-methyl-imidazole in presence of strong bases. This reaction was carried out in solvents such as dimethyl formamide, alcohols etc. resulting in about 72% yield.

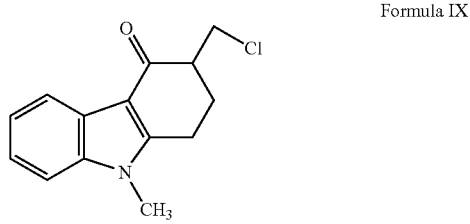

Formula IX

The '578 patent also talks about the oxidation of 2,3,4,9-tetrahydro-9-methyl-4-hydroxy-3-[(2-methyl-1H-imidazole-1-yl)methyl]-1H carbazol maleate of formula-XI using 2,3-dichloro-5,6-dicyano-1,4-benzoquinone (DDQ) in dry THF for the preparation of Ondansetron which according to the patent resulted in about 55% yield.

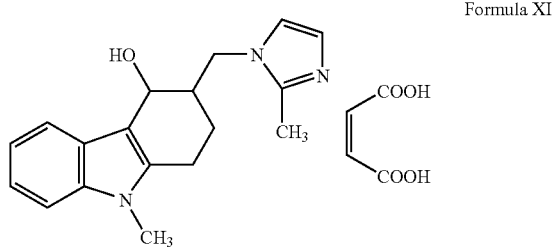

Formula XI

U.S. Pat. No. 5,478,949 discloses a multi-step process for preparing Ondansetron by providing a novel intermediate compound of Formula XII which activates the methyl group which is alpha to the oxo group of the carbazolone to facilitate introduction of imidazole heterocyclic ring with 2-methylimidazole to give a compound of Formula XIII which is in-turn converted into ondansetron in 75 to 87.3% yields according to the patent. Although the reaction proceeds well according to the patent, the process suffers from increased number of stages and the overall yields were not significant in comparison with the product patent ('578 patent) process.

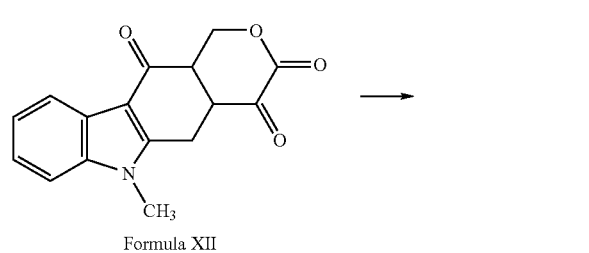

Formula XII

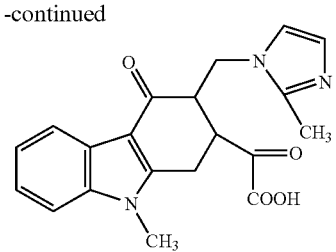

Formula XIII

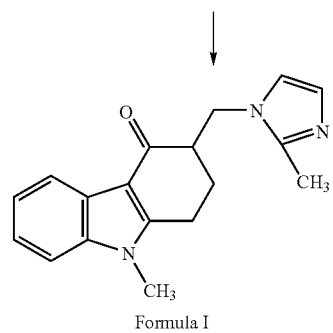

Formula I

U.S. Pat. No. 6,388,091 discloses an improvement for preparing Ondansetron wherein a Silyl enol ether of 1,2,3,9-tetrahydro-9-methyl-4H-carbazol-4-one of Formula XIV is alkylated with 1-(N,N-dialkylaminomethyl)-2-methylimidazole of Formula-XV (Scheme III) in presence of an organic solvent such as MDC, chloroform, acetonitrile, THF, dioxane, toluene, DMF, ethanol or mixture thereof resulting in an yield range of 81 to 86%. The process improves the yield of ondansetron but it lacks industrial applicability. One of the reasons being Silyl reagents are costly. Apart from this; the 1-(N,N-dialkylaminomethyl)-2-methylimidazole reagent has to be prepared, since it is not a commercially available reagent and therefore increases the number of steps in the process.

Scheme III

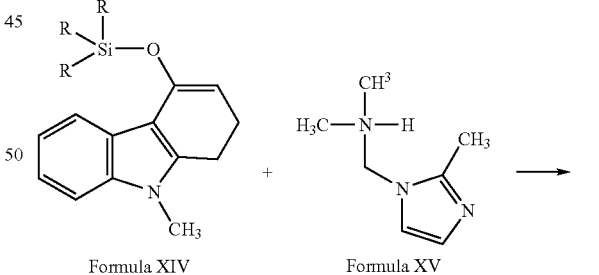

Formula XIV          Formula XV

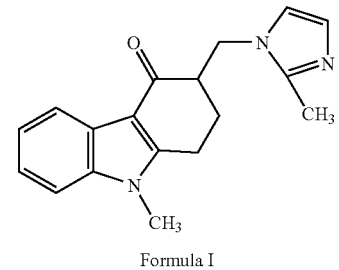

Formula I

In another prior art, U.S. Pat. No. 4,957,609, Ondansetron is prepared by a different route of synthesis wherein the last step is the closure of the central ring of 1,2,3,9-tetrahydrocarbazol-4-one ring system starting with a compound of Formula XVI where X is a hydrogen or a halogen atoms using copper or palladium catalyst. The solvent system used for the reaction includes DMF, N-methylpyrrolidone, HMPA, nitriles and alcohols. This process suffers from many disadvantages such as reaction specificity/regio-specificity in amino-methylation reaction and other side reactions and decomposition; accordingly the process is not suitable for industrial preparation of this pharmaceutical.

Scheme IV

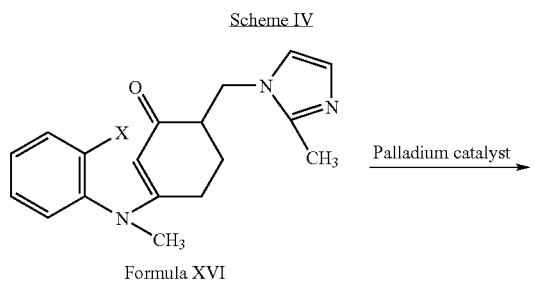

Formula XVI

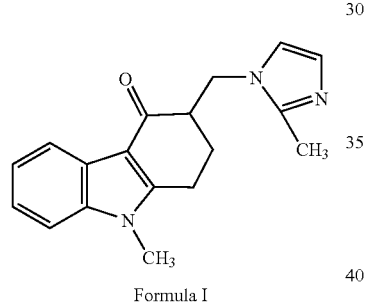

Formula I

Yet another U.S. Pat. No. 4,739,072 describes another cyclization process for preparing Ondansetron wherein the catalyst is different than '609 patent. In this process, the cyclization of the starting material, a hydrazine of a Formula-XVII, is induced with a Lewis acid in an aqueous or an organic solvent medium. This process also has disadvantages from the point of view of industrial applicability similar to those discussed in the above prior art.

Scheme V

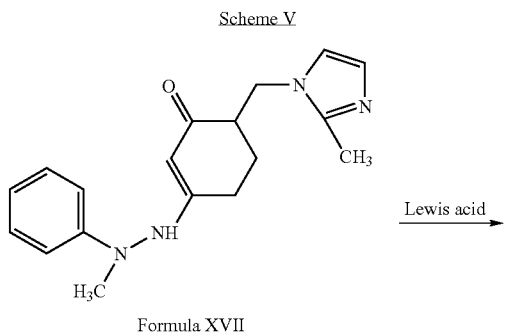

Formula XVII

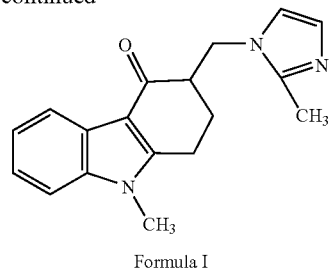

Formula I

The alpha amino-methylation of 4-oxo group of 1,2,3,9-tetrahydrocarbazole-4-one still remains a major difficulty and Patent No. CN 1105364 addresses this problem and discloses a preparative method for Ondansetron by activation of alpha-position of 4-oxo positions by enamine formation (Formula-XIX) and subsequent reaction with 2-methylimidazole, again increasing the number of stages in the production of ondansetron.

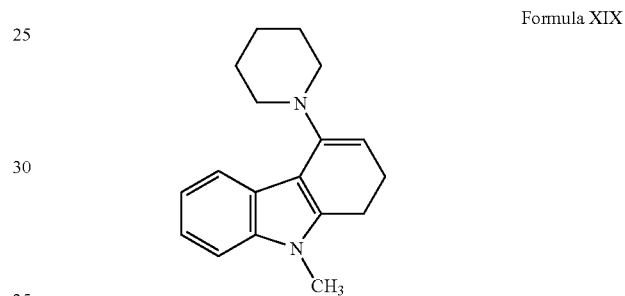

Formula XIX

Although various routes of synthesis available to a skilled synthetic chemist are disclosed in the product patent ('586 patent), several other prior arts (EP 59511, U.S. Pat. No. 4,983,621, EP191562, U.S. Pat. No. 4,822,881, KR923064, KR9832228, GB2152153821, ES2043535, RU2162695, RU2041876, CN1161966, CN1115760, CN1110970, CN1113239, CN1105364, CN1113913, CN1145902 etc.) are published and discuss improvements over the route disclosed in the said product patent and continued to work on to find improved process for Ondansetron of high purity in high yields.

WO 03093281 A1 discloses an improved process for preparation of Ondansetron over the processes disclosed in the '586 patent by introducing a solvent combination of water and dimethyl formamide instead of water alone in the transamination of compound of Formula-III with 2-methylimidazole and claimed to increase the yield from 80% to 96% but based on the penultimate intermediate 3-[(dimethylamine) methyl)]-1,2,3,9-tetrahydro-9-methyl-4H-carbazol-4-one as starting material. Therefore the overall yield from the 1,2,3, 9-tetrahydrocarbazole-4-one remains low.

It is apparent from the above discussion that considerable research is being carried out by synthetic chemists to develop a suitable industrial process for the preparation of Ondansetron to increase the yield and purity for which most of the synthetic routes were disclosed in the product patent itself. It can be understood that the major challenge in the preparative method is the introduction of side chain (methyl group) to the alpha position of the 4-oxo group of 1,2,3,9-tetrahydrocarbazole-4-one and the subsequent N-alkylation of 2-methylimidazole since most of the prior art patents concentrate their efforts on the final stage of the preparation of Ondansetron. The major drawback of most of the reported processes is that the Ondansetron prepared from the said intermediates of Formula-III, VIII and IX, results in lower yield having higher ratio of exo-methylene impurity apart from the difficulty in stirability of reaction mass due to tarry mass formation in amino-methylation reaction. Moreover the isolation of pure 3-[(dimethylamine)methyl)]-1,2,3,9-tetrahydro-9-methyl-4H-carbazol-4-one is considerably difficult due to the complex nature of the reaction mass resulting from the reported prior art processes. This ultimately leads to very poor yield and quality of the intermediate resulting in lower overall yield/purity of the Ondansetron from the compound of Formula-IV. The maneuvering of the amino-methylation reaction on an industrial scale is also a major concern. The present inventors have invested considerable efforts to tackle the problems associated with preparative methods of Ondansetron and have come up with an improved process which is the subject of the present invention.

OBJECTIVE OF THE INVENTION

Without limiting, the main objective of the present invention is to provide a simple, one pot industrial process for preparing Ondansetron of superior quality with high yield.

SUMMARY OF THE PRESENT INVENTION

Accordingly, there is provided a one-pot process for the preparation of Ondansetron starting from 1,2,3,9-tetrahydro-carbazole-4-one of Formula IV without isolating the intermediate of Formula-III and Formula-VIII, improving the rate of reaction, yield, selectivity, quality, scalability and the ease with which Ondansetron can be separated from the reaction mixture.

In one embodiment of the present invention, there is provided a solvent system for the Mannich amino-methylation of 1,2,3,9-tetrahydrocarbazole-4-one, which includes a combination of acetic acid and hydrocarbon solvents such as toluene, hexane, cyclohexane, etc. wherein the reaction proceeds at increased rate, giving high yield, without the formation of polymeric tarry materials. The reaction under the new conditions results into a mixture of intermediate compounds of Formula-III and Formula-VIII.

Another embodiment of the process is that it obviates the need for the isolation of these intermediates after distillation of the reaction medium/solvent mixture.

According to yet another embodiment of the present invention, the crude reaction mass containing intermediates of Formula-III and Formula-VIII are reacted without isolation in a single pot where, the trans-amination of compound of Formula III and Michael addition reaction of compound of Formula VIII with 2-methylimidazole are integrated to give ondansetron in a reaction medium chosen from combination solvents. The reaction proceeds at a rapid pace and completes in 5 to 8 hours under the given conditions. The integration of the two stages of reaction in a single pot is one of the special features of the present invention, which result in higher yield of Ondansetron in the range of 90 to 92% on the basis of starting 1,2,3,9-tetrahydrocarbazole-4-one Further one pot process is easy from the operational point of view.

Yet another embodiment of the reaction, according to the invention, is the simple isolation of Ondansetron substantially free of exo-methylene and other impurities in a one-pot reaction by purification with solvents such as dimethyl formamide, acetonitrile, acetonitrile-water, dimethyl formamide-water systems, in higher yield.

DETAILED DESCRIPTION OF THE INVENTION

The One-pot process of the present invention is described herein after in more details substantiating various embodiments and conditions of reaction for better understanding of the invention.

One-pot or single-pot reaction is hereinafter synonymous and means two or more processes are conducted in a single reaction vessel without isolating or purifying the resulting intermediates.

Mannich reaction herein refer to reactions where a secondary amine, formaldehyde and acid reacted to give a reactive species called Mannich base which is added to the alpha position of keto functional group.

Trans-amination herein after means, amination of acid addition salt of tertiary amine with another amine like imidazole, which forms more stable amino bond.

Exo-methylene impurity wherever entered in this specification is referred to 9-methyl-3-methylene-1,2,3,9-tetrahydro-4H-carbazol-4-one.

The present invention provides a one-pot process for preparing Ondansetron (I) starting from 1,2,3,9-tetrahydro-9-methyl-4H-carbazol-4-one. The 1,2,3,9-tetrahydro-9-methyl-4H-carbazol -4-one used in the present invention is prepared according to the process disclosed in Journal of Organic Chemistry, 1980, 45, 2938-2942.

In one aspect of the present invention, the Mannich reaction of 1,2,3,9-tetrahydro-9-methyl-4H-carbazol-4-one of Formula-IV with paraformaldehyde and N,N-dialkylamine hydrochloride is performed in a solvent system wherein the formation of polymeric tarry materials/impurity formation are limited/avoided to make the reaction mass easily stirrable, proceeds in a rapid pace and completes in 5 to 6 hours time. The reaction is carried out at elevated temperature ranging from 90° to 120° C., preferably in the range of 100° to 105° C.

According to the prior art, when this reaction is conducted in glacial acetic acid, reaction is sluggish and leads to formation of sticky polymeric material/impurities which necessitates the isolation, purification of 3-[(dimethylamine)methyl)]-1,2,3,9-tetrahydro-9-methyl-4H-carbazol-4-one in order to carry out the subsequent reaction resulting into poor yield of the penultimate intermediate apart from problems of maneuvering on large scale. The reaction time is very high in the order of 40 to 47 hours for its completion.

An advantage of the present solvent system is that the reaction mass is homogeneous making easy operation on large scale, the rate of reaction and the reaction specificity are significantly increased. The purity of the intermediates is considerably high to make the process to be integrated for the final molecule formation in the same pot without isolation/purification in the preceding step.

In the process of the present invention, it is observed that the reaction yields two intermediates namely, 3-[(dimethylamine)methyl)]-1,2,3,9-tetrahydro-9-methyl-4H-carbazol-4-one of Formula-III and 9-methyl-3-methylene-1,2,3,9-tetrahydro-4H-carbazol-4-one of Formula-VIII devoid of any major impurity and can be used as such for subsequent transformation. On completion of the reaction, i.e. disappearance of 1,2,3,9-tetrahydro-9-methyl-4H-carbazol-4-one, the reaction solvents are conveniently distilled to obtain concentrated reaction mass containing the said intermediates in a ratio from 70:30 to 50:50 as analyzed by TLC. (Scheme VI)

Scheme VI

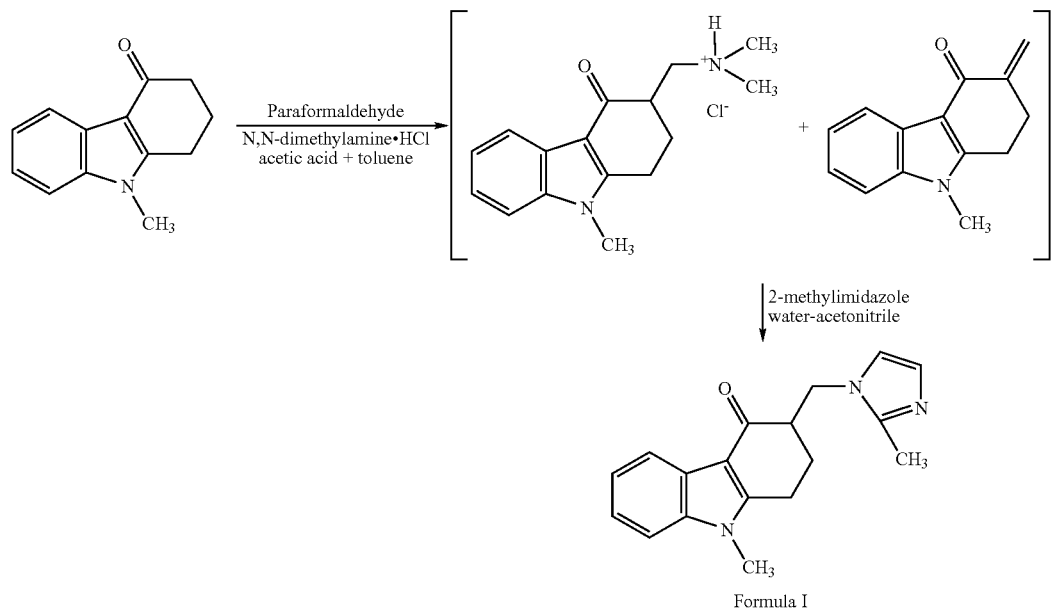

Formula I

The secondary amine used in the Mannich reaction is selected from a compound of general Formula HNR1R2 wherein R1 and R2 are independently alkyl groups, R1R2 together are cyclic alkyl groups. Examples of secondary amines are N,N-dimethylamine, N,N-diethylamine, N,N-diisopropylamine, piperidine, morpholine, pyrrolidine etc. The secondary amine preferably and advantageously used in the invention are N,N-dimethylamine and N,N-diisopropylamine. The secondary amine may be used as free base or its salt such as hydrochloride. If the amine in the free form is used then a molar equivalent of an inorganic acid like hydrochloric acid is used along with paraformaldehyde. The hydrochloric acid may be introduced in the gaseous form by purging or in its solution form.

The solvent system for the above reaction is selected from the group consisting of acetic acid-toluene, acetic acid-hexane, acetic acid-cyclohexane, acetic acid-heptane, acetic acid-xylene, etc. The ratio of the solvent system i.e. acetic acid to hydrocarbon solvents is in the range of 90:10 to 60:40, preferable range is 80:20. The preferable solvent system is acetic acid-toluene in a ratio of 80:20. In the process the reactants and the intermediate products formed are in a homogeneous condition thereby facilitating a rapid reaction without forming considerable impurities. In the process, the solvent system may be previously prepared before addition of the reactants or the reactants may be suspended/dissolved in one of the solvents and the second solvent may be added subsequently before heating reaction mass. The reactants may be added into the solvents system at ambient conditions or at elevated temperatures. The reaction can also be performed in a pressurized vessel at a lower temperature than the one that is carried out at ambient pressure.

In the process conditions of the present invention the reaction of paraformaldehyde, N,N-dimethylamine hydrochloride and 1,2,3,9-tetrahydrocarbazole-4-one results into two compounds namely 3-[(dimethylamine)methyl)]-1,2,3,9-tetrahydro-9-methyl-4H-carbazol-4-one of Formula-III and 9-methyl-3-methylene-1,2,3,9-tetradydro-4H-carbazol-4- one of Formula-VIII which is advantageously integrated to the transamination and Michael addition reaction with 2-methylimidazole to give the same product i.e. Ondansetron, in higher yield in the same pot without isolation/purification of the preceding reaction mass. The said intermediates undergo transamination and Michael type addition reaction respectively with 2-methylimidazole in the same pot in a suitable solvent system at elevated temperatures. The reaction proceeds at an accelerated rate to form ondansetron from both the intermediates and completes in 5 to 8 hours as compared to the longer duration, viz: 20 to 47 hours, reported in prior art.

The 2-methylimidazole is preferably used in excess relative to the starting material, 1,2,3,9-tetrahydrocarbazole-4-one (IV), preferably in a molar excess of about 5-6 molar equivalent with respect to starting material.

The advantage of the present invention is increased rate of reaction achieved without sacrificing yield or producing new side products. The exo-methylene compound is almost consumed in the reaction so that the exo-methylene impurity is limited in the final Ondansetron hydrochloride salt to an amount of less than 0.1%.

In the above reaction process of the present invention wherein compound of Formula-III and VIII are reacted with 2-methylimidazole, the preferable solvents used are selected from acetonitrile, water, dimethyl formamide, dimethylacetamide, acetonitrile-water, dimethylformamide-water, dimethyl acetamide-water etc. The basic need of the reaction medium is that both reactants and products should be soluble in the reaction medium so that reaction is rapid and no undue side reaction take place during the reaction. The preferable solvent system is acetonitrile-water, or dimethylformamide-water. The ratio of water to the organic solvent is selected from a range of 10 to 60% organic solvent and 90 to 40% water.

The reaction of compound of Formula-III and VIII with 2-methylimidazole is carried out at a temperature range of 90-110° C., preferably 95-100° C. and the reaction completes in 5 to 8 hours. On completion of the reaction, crude ondansetron is isolated conveniently from the reaction medium by cooling to precipitate the product. The yield of ondansetron based on the starting material 1,2,3,9-tetrahydrocarbazole-4-one (IV) is considerably significant and is in the range of 90 to 92%.

The crude Ondansetron is purified by crystallization procedure from suitable solvents. The solvents for crystallization are selected from aprotic polar solvents such as N,N-dimethyl formamide, acetontrile, N-methylpyrrolidone. The preferred solvent is dimethyl formamide. The crude Ondansetron is dissolved in the crystallizing solvents at elevated temperature like 90 to 95° C. and progressively cooled to crystallize the pure product. The preferable concentration of ondansetron relative to the solvent is in an amount of about 5 to 25 ml. per gram of Ondansetron and more preferably about 10 ml. per gram. In the process crude Ondansetron is dissolved in DMF at 90-95° C. to get clear solution, optionally filtering to remove insoluble, which upon slow cooling accelerated the crystallization of the said product. The crystal form of ondansetron free base so prepared is identical with Form B reported in WO-2004063189.

The Ondansetron obtained by the crystallization according to this procedure is almost free from exomethylene carbazolone impurity i.e. less than 0.1% (based on HPLC analysis) complying to the pharmacopoeia specifications. The isolated Ondansetron also may be converted to a pharmaceutically acceptable acid addition salt preferably a hydrochloride salt using techniques well known in the art like purging hydrochloric acid gas or providing an alcoholic solution of dry HCl into a solution of ondansetron free base in alcoholic solvents such as isopropyl alcohol to precipitate pure Ondansetron hydrochloride salt.

The following non-limiting examples presented to illustrate the best mode of carrying out the process of the present invention. The examples are not limited to the particular embodiments illustrated herein but include the permutations, which are obvious set forth in the description.

EXAMPLES

Example 1

50 Kg 1,2,3,9-tetrahydro-9-methyl-4H-carbazol-4-one, 25 kg N,N-dimethylamine hydrochloride and 10 kg paraformaldehyde were charged into a reaction vessel containing a combination of acetic acid 400 litre and toluene 100 litre. Under stirring, the mass was heated to a temperature of 100 to 105° C. for a period of 3.5 hours. On disappearance of 1,2,3,9-tetrahydro-9-methyl-4H-carbazol-4-one on TLC analysis, the acetic acid-toluene was distilled under vacuum at 60-65° C. To the concentrated reaction mass, 104 kg 2-methylimidazole, 100 litre acetonitrile, 400 litre water were added and heated to 80 to 85° C. for 6 hours. The reaction mass was then slowly cooled to 20 to 25° C. Filtered and washed with 500 litre water which upon drying gave 68 kg ondansetron base. Melting point 229 to 231° C.

Example 2

50 Kg 1,2,3,9-tetrahydro-9-methyl-4H-carbazol-4-one, 25 kg N,N-dimethylamine hydrochloride and 10 kg paraformaldehyde were charged into a reaction vessel containing a combination of acetic acid 400 litre and toluene 100 litre. Under stirring the mass was heated to a temperature of 100 to 105° C. for a period of 3.5 hours. On disappearance of 1,2,3,9-tetrahydro-9-methyl-4H-carbazol-4-one on TLC analysis, the acetic acid-toluene was distilled under vacuum at 60-65° C. To the concentrated reaction mass, 104 kg 2-methylimidazole, 50 litre acetonitrile, 450 litre water were added and heated to 80 to 85° C. for 6 hours. The reaction mass was then slowly cooled to 20 to 25° C. Filtered and washed with 500 litre water which upon drying gave 68.5 kg ondansetron base. Melting point 229 to 231° C.

Example 3

50 Kg 1,2,3,9-tetrahydro-9-methyl-4H-carbazol-4-one, 25 kg N,N-dimethylamine hydrochloride and 10 kg paraformaldehyde were charged into a reaction vessel containing a combination of acetic acid 400 litre and toluene 100 litre. Under stirring the mass was heated to a temperature of 100 to 105° C. for a period of 3.5 hours. On disappearance of 1,2,3,9-tetrahydro-9-methyl-4H-carbazol-4-one on TLC analysis, the acetic acid-toluene was distilled under vacuum at 60-65° C. To the concentrated reaction mass, 104 kg 2-methylimidazole, 100 litre N,N-dimethylformamide, 400 litre water were added and heated to 90 to 95° C. for 6 hours. The reaction mass was then slowly cooled to 20 to 25° C. Filtered and washed with 500 litre water which upon drying gave 67 kg ondansetron base. Melting point 229 to 231° C.

Example 4

50 Kg 1,2,3,9-tetrahydro-9-methyl-4H-carbazol-4-one, 25 kg N,N-dimethylamine hydrochloride and 10 kg paraformaldehyde were charged into a reaction vessel containing a combination of acetic acid 400 litre and toluene 100 litre. Under stirring the mass was heated to a temperature of 100 to 105° C. for a period of 3.5 hours. On disappearance of 1,2,3,9-tetrahydro-9-methyl-4H-carbazol-4-one on TLC analysis, the acetic acid-toluene was distilled under vacuum at 60-65° C. To the concentrated reaction mass, 104 kg 2-methylimidazole, 50 litre N,N-dimethylformamide, 400 litre water were added and heated to 90 to 95° C. for 6 hours. The reaction mass was then slowly cooled to 20 to 25° C. Filtered and washed with 500 litre water which upon drying gave 68 kg ondansetron base. Melting point 229 to 231° C.

Example 5

Purification 100 kg ondansetron free base was charged into a reaction vessel, further 1000 litre dimethylformamide was added and the reaction mass was heated to 90° C. for 1.0 hour. After complete dissolution of ondansetron the solution was cooled to a temperature of 30° C. and further chilled to 0 to 5° C. The crystallized product was filtered and dried to give 80 kg ondansetron free base. A second crop of 5-7 kg was recovered from the mother liquor. The crystal structure is identical with Form B reported in WO-2004063189

We claim:

1. A one-pot process for preparing a compound of Formula-I

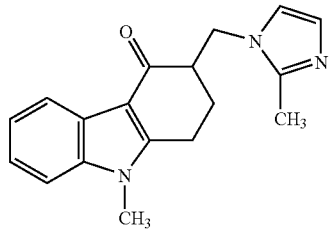

Formula I comprising the steps of
a) reacting a compound of Formula IV

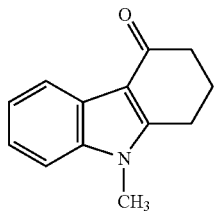

Formula IV with HNR1R2, or its salt, and paraformaldehyde in a solvent medium of acetic acid and hydrocarbon solvent to give a mixture of intermediate compounds of Formula III

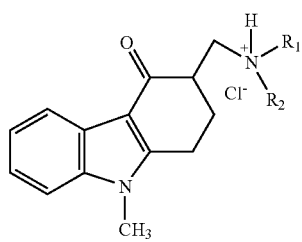

Formula III and Formula VIII

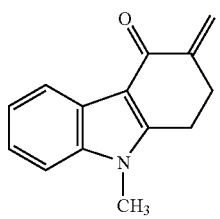

Formula VIII wherein R1 and R2 are (i) independent alkyl groups, (ii) together forms a cyclic alkyl group, or (iii) together forms morpholine; and b) reacting said mixture of intermediate compounds with 2-methyl imidazole in a solvent system to obtain the compound of Formula I in the same pot.

2. The process of claim 1, wherein said HNR1R2 are selected from N, N-dimethylamine, N, N-diethylamine, N, N-diisopropylamine, morpholine, piperidine, pyrrolidine or their salts.

3. The process of claim 1, wherein said HNR1R2 is N, N-dimethylamine hydrochloride or N, N-diisopropylamine hydrochloride.

4. The process of claim 1, wherein the solvent medium of step a) is acetic acid-toluene, acetic acid-hexane, acetic acid-heptane, acetic acid-xylene, or acetic acid-cyclohexane.

5. The process of claim 4, wherein the ratio of solvents of acetic acid and hydrocarbon solvents of said solvent system is about 60:40 to 90:10.

6. The process of claim 4, wherein the ratio of solvents of acetic acid and hydrocarbon solvents of said solvent system is about 80:20.

7. The process of claim 1, wherein water content in the reaction solvents is about 0.1% to not more than 0.2%.

8. The process of claim 1, wherein the reaction is performed in anhydrous condition.

9. The process of claim 1, wherein the reaction of step a) is carried out at a temperature of about 90 to 120° C.

10. The process of claim 1, wherein the ratio of the compound of Formula III to the compound of Formula VIII is about 70:30 to 50:50.

11. The process of claim 1, wherein the ratio of compound of Formula III to Formula VIII is about 60:40.

12. The process of claim 1, wherein the reaction of step b) is carried out in organic solvent-water system.

13. The process of claim 1, wherein the solvent system of step b is acetonitrile, water, N,N-dimethylformamide, N-methylpyrrolidone, acetonitrile-water, N,N-dimethyl formamide water, or N-methylpyrrolidone-water.

14. The process as claimed in claim 12, wherein the organic solvent-water system is acetonitrile-water or dimethyl formamide-water.

15. The process of claim 12, wherein the ratio of the organic solvent to water in said organic solvent-water system is about 10:90 to 20:80.

16. The process of claim 1, wherein the ratio of Formula III to Formula VIII in the crude mixture is about 70:30 to 50:50.

17. The process of claim 1, wherein the reaction of step b) is performed at a temperature of about 80 to 110° C.

18. The process claim 1, wherein the 2-methyl imidazole is used in molar excess relative to starting material of Formula IV.

19. The process of claim 18, wherein the 2-methyl imidazole is about 2 to 6 molar equivalent relative to the compound of Formula IV.

20. The process of claim 18, wherein the reactant 2-methyl imidazole is 5 molar equivalent relative to starting material of Formula IV.

21. The process of claim 1, wherein steps a) and b) takes place in the same pot.

22. A one-pot process for preparing a compound of Formula-I

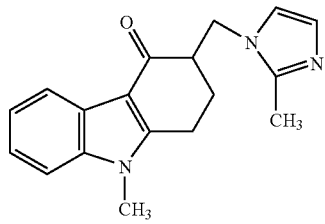

Formula I comprising the step of reacting a mixture of compounds of Formula III

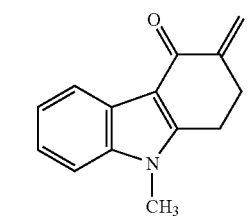

Formula III and Formula VIII

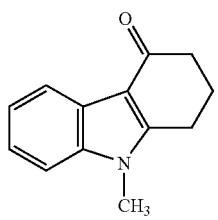

Formula VIII with 2-methyl imidazole in a medium of dimethyl formamide-water or acetonitrile-water.

23. The process of claim 22, wherein the ratio of Formula III to Formula VIII is about 70:30 to 50:50.

24. The process of claim 22, further comprising the step of separating the compound of Formula I from the reaction mass.

25. The process of claim 24, wherein the separating step comprises
   i) cooling the compound of Formula I from the reaction mass;
   ii) filtering to remove the free base of the compound of Formula I from the reaction mass;
   iii) forming a solution of the free base of the compound of Formula I in an aprotic polar solvent; and
   iv) progressively cooling said solution of step iii) to obtain the compound of Formula I in solid state.

26. The process of claim 25, wherein the aprotic polar solvent is DMF, acetonitrile, or N-methylpyrrolidone.

27. The process of claim 22, wherein the compound of formula I prepared is substantially free from 9-methyl-3-methylene-1, 2,3,9-tetrahydro-4H- carbazol -4-one impurity or at least less than 0.1%.

28. The process of claim 22, further comprising the step of converting the compound of Formula I to a hydrochloride salt.

29. A process for preparing a compound of Formula-I

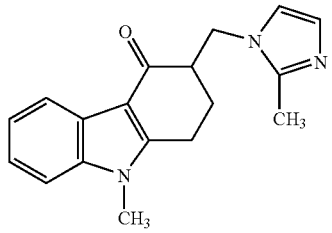

Formula I comprising the steps of
   a) reacting a compound of Formula IV

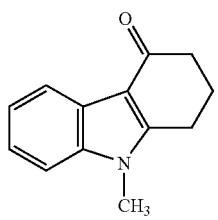

Formula IV with HNR1R2, or its salt, and paraformaldehyde in a solvent medium of acetic acid and hydrocarbon solvent to give a mixture of intermediate compounds of Formula III

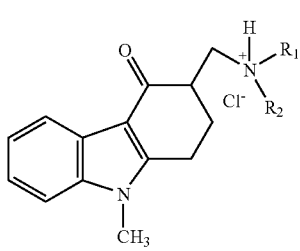

Formula III and Formula VIII

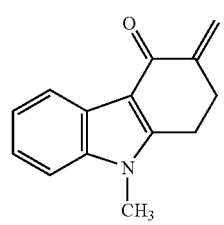

Formula VIII wherein R1 and R2 are (i) independent alkyl groups, (ii) together forms a cyclic alkyl group, or (iii) together forms morpholine; and
   b) reacting said mixture of intermediate compounds with 2-methyl imidazole in a solvent system to obtain the compound of Formula I.

* * * * *